United States Patent [19]
Mayton

[11] Patent Number: 5,309,926
[45] Date of Patent: May 10, 1994

[54] RESTRAINT FOR CHANGING AN INFANT

[76] Inventor: Lisa H. Mayton, 6346 McCollum La., Acworth, Ga. 30301

[21] Appl. No.: 856,517

[22] Filed: Mar. 24, 1992

[51] Int. Cl.⁵ .......................... A61B 19/00; A61F 5/37
[52] U.S. Cl. ..................................... 128/869; 128/876
[58] Field of Search .............................. 128/874–876, 128/869, 870, 100.1; 602/19, 18, 17

[56] References Cited

U.S. PATENT DOCUMENTS

| | | | |
|---|---|---|---|
| D. 837,373 | 12/1906 | Akers | 128/876 |
| 2,102,281 | 12/1937 | Pringle | 128/875 |
| 2,332,035 | 10/1943 | Wickman | 128/876 |
| 2,486,114 | 10/1949 | Cataldo | 128/876 |
| 2,619,958 | 12/1952 | Day | 128/876 |
| 3,035,278 | 5/1962 | Golding | 5/317 |
| 3,100,484 | 8/1963 | Berl | 128/876 |
| 3,779,540 | 12/1973 | Boudreau | 269/328 |
| 4,224,935 | 9/1980 | Metelnick | 602/3 |
| 4,858,625 | 8/1989 | Cramer | 128/872 |
| 5,086,758 | 2/1992 | Schiek | 128/876 |
| 5,086,759 | 2/1992 | Buddingh | 602/19 |
| 5,105,828 | 4/1992 | Grant | 128/876 |

FOREIGN PATENT DOCUMENTS

| | | | |
|---|---|---|---|
| 0682773 | 10/1939 | Fed. Rep. of Germany | 128/875 |
| 2585237 | 1/1987 | France | 128/876 |

*Primary Examiner*—Michael A. Brown
*Attorney, Agent, or Firm*—Michael Drew

[57] ABSTRACT

A restraint for changing an infant (10) has a major band (20) and a restricting band (40). The ends of the major band (20) are adapted to wrap around a surface (11) upon which an infant (13) will be changed and connect to one another. A second band, a restricting band, (40) has two ends (41, 44) and attaches to the top surface of the major band (20). One end (41) of the restricting band (40) may be permanently affixed to the major band (20) while the second end, or free end, (44) of the restricting band (40) attaches to the major band (20) by means of a detachable fastener (46). The points of attachment of the restricting band (40) to the major band (20) define an infant securement area (30) which holds the infant (13) to be changed. Each end of the major band (20) may be split (22, 23) so as to accommodate obstructions associated with a changing surface (11) with which the restraint (10) will be used.

14 Claims, 2 Drawing Sheets

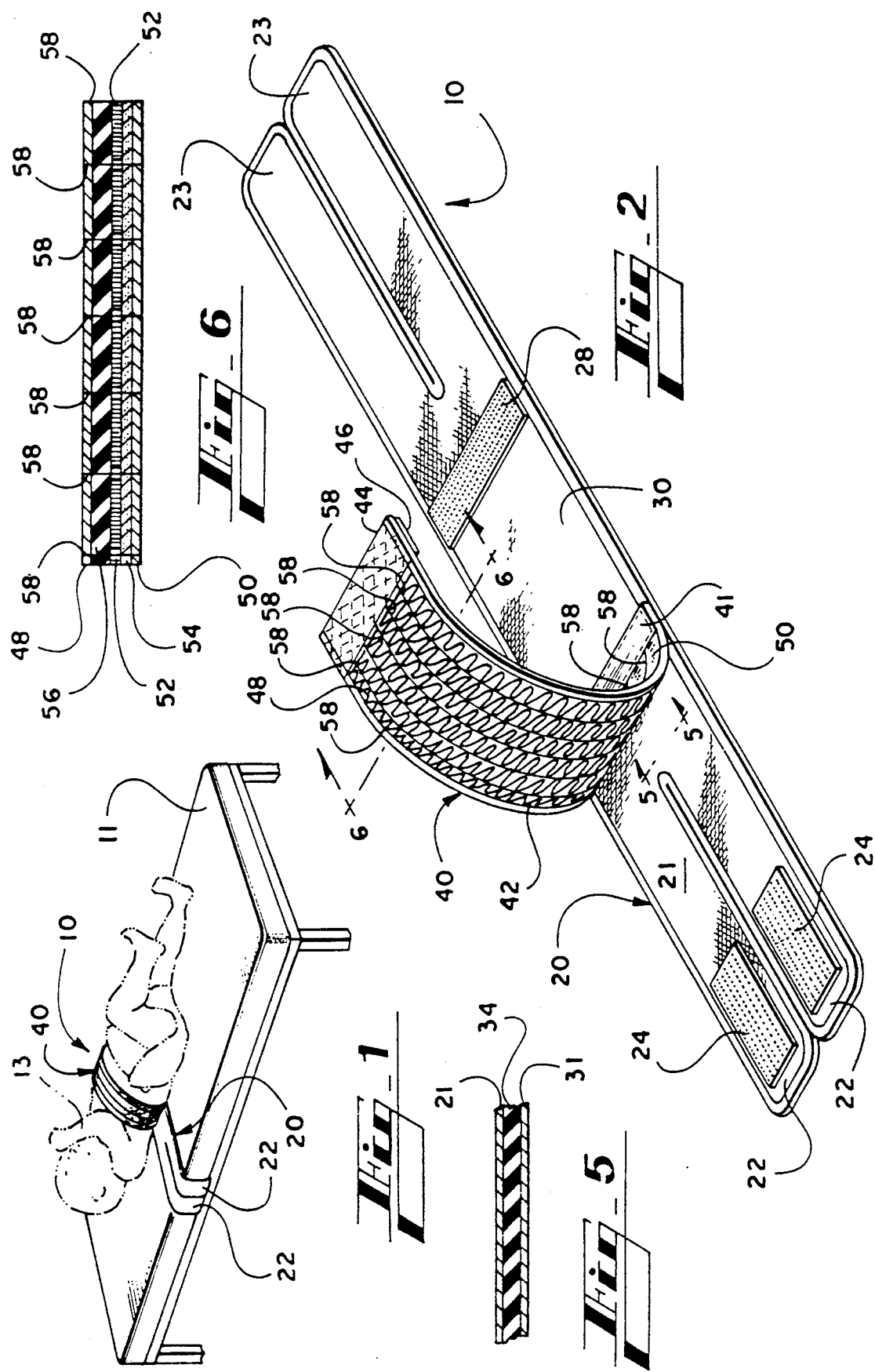

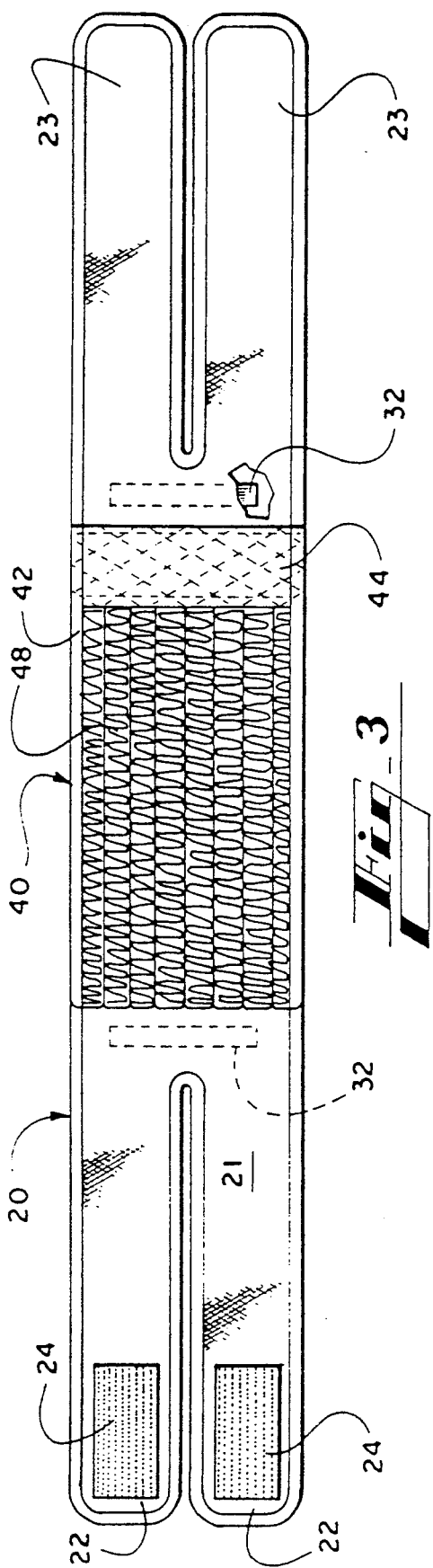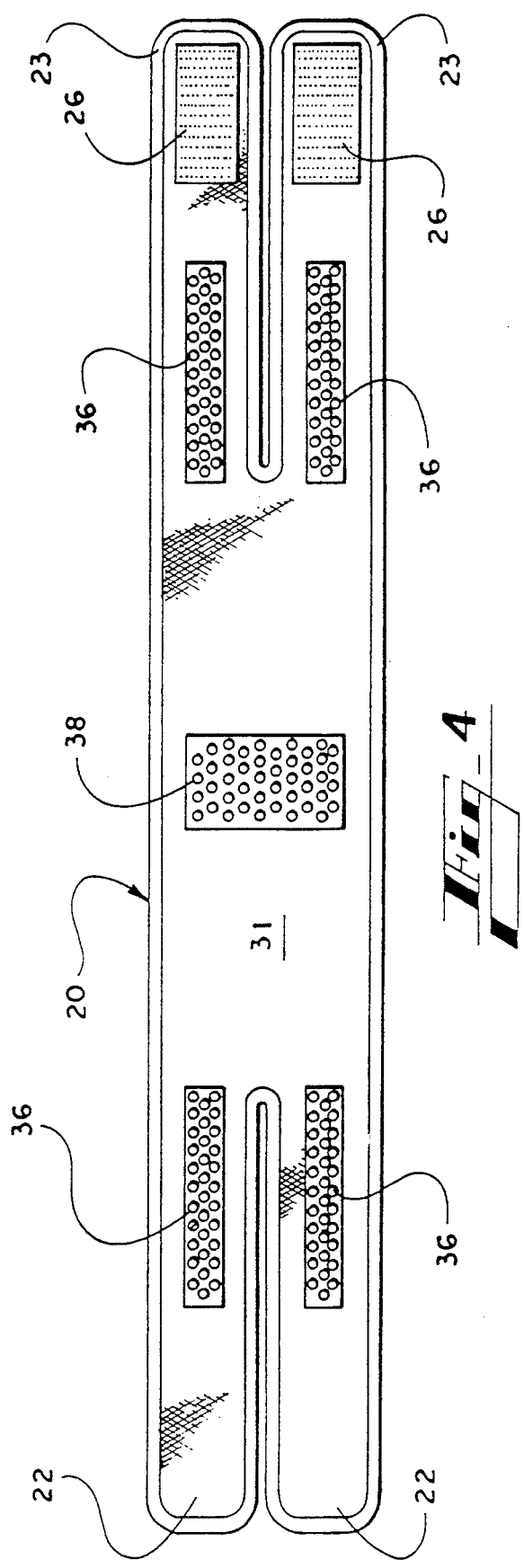

RESTRAINT FOR CHANGING AN INFANT

TECHNICAL FIELD OF THE INVENTION

The present invention relates to a device for restricting movement of an infant while the infant is being changed.

BACKGROUND OF THE INVENTION

Infants generally are prone to quick, sudden squirmy movements while they are being changed. It is important in changing infants that movement of the infant be restricted so that diapers and clothing may be properly applied, so that medication may be properly applied and to prevent the infant from falling from the surface upon which it is being changed or otherwise become injured due to unexpected movements. It is particularly important that movement of an infant be restricted when the infant is being changed upon a changing table because changing tables are normally narrow and elevated well above the floor. An infant is very likely to be injured if it falls from a changing table. In restricting the movement of an infant during changing, if a restraining device is used, it is also important that the infant not be injured by the restraining device. Restricting movement while minimizing the chance for injury to an infant is a problem because infants are generally small and delicate. It is also desirable that the infant be kept as comfortable as possible during changing so that the infant's discomfort does not promote undesirable movement. Comfort is also desirable in the best interest of the child. Thus, it would be useful to have a device for restricting movement of an infant during changing that enhances the changing process, that minimizes the chance for injury to the infant and that maximizes comfort for the infant.

SUMMARY OF THE INVENTION

It is an object of the invention to provide a means for restricting movement of an infant during changing.

It is a further object of the invention to provide a means for restricting movement of an infant during changing that enhances the changing process, that prevents the child for falling from the changing surface and that is comfortable for the infant.

In the present invention, a restraint for changing an infant has a major band and a restricting band. The ends of the major band are adapted to wrap around a surface upon which an infant will be changed and connect to one another. A second band, a restricting band, has two ends and attaches to the top surface of the major band. One end of the restricting band may be permanently affixed to the major band while the second end of the restricting band attaches to the major band by means of a detachable fastener. The points of attachment of the restricting band to the major band define an infant securement area which holds the infant to be changed. Each end of the major band may be split so as to accommodate obstructions associated with a changing with which it will be used.

Other aspects, objects, features, and advantages of the present invention will become apparent to those skilled in the art upon reading the detailed description of preferred embodiments.

BRIEF DESCRIPTION OF THE DRAWINGS

FIG. 1 is an isometric illustration of a restraint for changing an infant according to a preferred embodiment of the invention, shown mounted upon a changing surface and holding an infant.

FIG. 2 is an isometric illustration of the invention of FIG. 1 detached from the changing surface and without the infant of FIG. 1.

FIG. 3 is a top plan view of the invention of FIG. 1.

FIG. 4 is a bottom plan view of the invention of FIG. 1.

FIG. 5 is a partial sectional view of the invention of FIG. 2 taken along line V—V.

FIG. 6 is a partial sectional view of the invention of FIG. 2 taken along line VI—VI.

DETAILED DESCRIPTION OF PREFERRED EMBODIMENTS OF THE INVENTION

While the specification concludes with claims particularly pointing out and distinctly claiming the subject matter which is regarded as the present invention, the invention will now be described with reference to the following description of embodiments taken in conjunction with the accompanying drawings. Throughout the drawings the same numerals refer to like features.

In a preferred embodiment of the invention two bands form the essential components of a restraint for changing an infant. Referring first to FIG. 1, therein is shown a restraint for changing an infant 10 according to a preferred embodiment of the invention. The restraint 10 has a major band 20 which engages the surface upon which an infant 13 is changed. In the depiction of the preferred embodiment shown in FIG. 1, the changing surface is a changing table 11. A second band, that is, the restricting band 40, is shown engaging the midsection of the infant 13.

Referring now to FIG. 2, more details of the restraint 10 are illustrated. As previously mentioned, the main components of the restraint 10 are the major band 20 and the restricting band 40. The major band 20 attaches the restraint 10 to the changing table 11, and the restricting band 40 immobilizes the infant 13.

The width of the major band 20 and the restricting band 40 is important to obtain optimum results from the restraint 10. The width of the restricting band 40 must be sufficient to prevent the infant 13 from moving laterally on the changing surface and also to prevent the infant 13 from moving laterally in a clockwise or counterclockwise direction. A wide restricting band 40 also helps prevent the infant 13 from easily turning over. However, if the width is too great too much of the infant is covered to facilitate changing. To allow access to the full trunk area and lower torso of the infant, the width of the restricting band 40 should be less than the length of the midsection of the infant 13. Additionally, if the width of the restricting band 40 is too great unnecessary materials are used to construct the restraint 10, unnecessarily increasing its cost. The restricting band 40 cannot be too narrow because it may be inefficient as far as restricting movement. A band which is too narrow is also likely to abrade the skin of the infant 13, pinch body parts or cause undue pressure to be placed upon body parts as the infant attempts to move. Although any width which adequately covers the midsection of the infant 13 while still allowing access for changing is sufficient, a suitable width is about six inches.

The major band 20 must be wide enough to firmly encircle the changing surface, that is, changing table 11. The major band 20 must also be wide enough to provide adequate support for the attachment of the restricting band 40. Optimum support of the restricting band 40 is achieved when where it attaches to the major band 20 is at least as wide as the restricting band 40. If the area of attachment on the major band 20 is substantially less than the width of the restricting band 20, the major band 20 will be subject to greater torque or leverage by the restricting band 40 as the infant 13 attempts to move about.

Although in FIG. 1 the changing surface is depicted as a changing table 11, the restraint 10 is adapted for use upon any structure which the major band 20 may encircle. For example, the major band 20 may be wrapped and secured around the thighs of a seated individual or a bench.

The split ends, or appendages, 22, 23 of the major band 20 enable the restraint 10 to accommodate many variations in structure of changing surfaces because although the major band 20 itself is wide the joining ends 22, 23 are narrow enough to fit through small openings to pass under and through the supports of a changing surface. For example, although the changing table 11 depicted in FIG. 1 only has support legs at the corners, some changing tables have support legs at the center or at other points where it is desirable to pass the major band 20 under the changing surface. The split ends 22, 23 can easily be maneuvered to accommodate obstructions such as support legs. The ends 22, 23 of the major band 20 are joined by any suitable adjustable means. A hook and loop type fastener such as Velcro ® strips work well in the invention because such a fastener provides a means for rapid securement and infinite incremental adjustment. The Velcro strips 24 form a part of the hook and loop fastener. Corresponding Velcro strips 26 on the opposite end of the major band 20 are discussed further below. Referring now momentarily to the partial sectional view of FIG. 5, the major band 20 may be constructed from combinations of many materials, however, a combination which works well in the preferred embodiment is a top surface 21 of fabric and a bottom surface 31 of fabric (not seen in the view of FIG. 2) which sandwiches between them a layer of padding 34 such as bonded polyester. The result is a major band 20 which is comfortably quilted.

The restricting band 40 is essentially an elasticized belt-like portion 42 with one end affixed to the major band and the other end, a free end attachable to the major band. In the preferred embodiment of the restraint 10 illustrated, one end 41 of the restricting band 40 is shown permanently affixed to the major band 20 while the free end 44 is attachable to the major band 20 by Velcro material 46 which engages a corresponding portion of Velcro material 28 on the major band 20. The two pieces of Velcro material 28, 46 form a Velcro fastener. It is possible to have both ends attachable by fasteners but it is easier to secure an infant 13 when an attached end 41 is fixed in place and only a free end 44 need be secured. By placing the fastening portions 28, 46 so that the free end, or fastening end, 44 of the restricting band fastens to the side of an infant 13 placed in the restraint 10, the attention of the infant 13 is not easily directed to the fastener and thus the infant 13 will not easily attempt to undue the fastening portion. As similarly mentioned in the description of a fastening mechanism for the major band 20, the use of a hook and loop fastener such as Velcro enables the restricting band 40 to be quickly attached to the major band 20 and adjusted in infinite increments. Referring now momentarily to the partial sectional view of FIG. 6, the restricting band 40 may be constructed from many combinations of materials, however, a combination which works well in the preferred embodiment of the restraint 10 is a top surface 48 of fabric and an under-surface 50 of fabric which sandwiches between them elastic strips 52 of the type commonly used in clothing, a polyester inner liner 54 such as non-woven, fused fabric used in the clothing industry and a padding material 56 such as bonded polyester next to the outer layer of fabric, 48 all of which generally run the length of the elasticized belt 42. The purpose of the elastic strips 52 is to produce elasticity in the restricting band 40 to help secure the infant 13. The polyester inner lining 54 provides reinforcement that helps alleviate bunching or widthwise deformation of the restricting band 40, particularly as the infant 13 attempts to move. The bonded polyester 56 is padding added for comfort.

Referring now to FIG. 3, a plan view of the top surface of the restraint 10, in addition to the features discussed immediately above, therein is illustrated a reinforcing strip 32 embedded widthwise in the major band 20 adjacent each side of the restricting band 20. The reinforcing strips 32 prevent widthwise deformation and bunching of the major band 20. A suitable material for the reinforcing strips 32 is known in the fabric industry as "boning." The Velcro material 24 on the split ends 22, or appendages, are located thereon to engage fasteners on the opposite end of the major band 20 of the restraint 10.

Referring now to FIG. 4, the view of the bottom surface 31 of major band 20 shows the Velcro material 26 on the split ends 23 that connects with the corresponding Velcro material 24 on the top surface of the split ends 22 at the opposing end of the major band 20. Single-fold or double-ply fabric is suitable for the surfaces 21, 31, 48, 50 of the respective bands 20, 40. Adherence of the major band 20 with respect to a table 11 or other changing surface is desirable to prevent the major band 20 of the restraint 10 from slippling with respect to the table 11 when a child 13 is being held by the restraint 10. Adherence, or non-slippage, may be achieved by providing an area on the bottom, or rear, surface 31 of the major band 20 that deters slippage of the major band 20 with respect to a changing surface 11 by gripping the changing surface 11. The gripping ability of the back 31 of the major band 20 may be achieved by providing areas which have raised or furrowed surfaces which are less likely to slip with respect to a surface which is engaged. Raised or furrowed areas are simply achieved by providing a surface having alternating raised or protruding areas extending from the surface. The bottom, or back, surface 31 of the major band 20 has areas which enhance adherence of the major band 20 to the changing surface. Adherence is enhanced through the use of friction-enhancing material such as raised, ribbed, noduled or otherwise corrugated areas. These corrugated areas grip the changing surface upon which the major band 20 rests. A suitable material for the corrugated strips 36, 38 shown is vinyl-dotted fabric. Vinyl-dotted fabric essentially has rubberized dots, or nodules, protruding from fabric. The corrugated areas of protruding dots 36 near either end 22, 23 of the major band 20 help prevent sliding of the major band 20 with respect to the changing surface 11. The middle area of protruding dots 38 helps prevent slipping of the portion of the major band 20 under the infant 13.

To use the restrain 10, the ends 22, 23 of the major band 20 are wrapped around the changing surface 11. If the changing surface has an obstruction, the split ends 24, 26 may be placed on either side of the obstruction or otherwise maneuvered around the obstruction. The major band 20 is secured by joining Velcro material 24, 26 the ends 22, 23. The infant 13 is placed upon the major band 20 over the infant securement area 30. The restricting band 40 is gently placed over the mid-section of the infant 13 and the restricting band 40 is secured by fastening Velcro material 46 at the free end 44 of the restricting band 40 to the Velcro material 28 on major band.

The restraint 10 not only prevents an infant 13 from falling from the changing surface but also facilitates changing by restricting movement of the infant 13 due to the wide restricting band 40. The infant 13 generally cannot roll over or twist. The elasticity 42 employed in the restricting band 40 helps make the infant 13 more comfortable while its movement is restricted and also helps to firmly restrict the infant's 13 movements that might otherwise allow the infant 13 to remove itself from within the restricting band 40.

As should be apparent from the foregoing specification, the invention is susceptible of being modified with various alterations and modifications which may differ from those which have been described in the preceding specification and description. Accordingly, the following claims are intended to cover all alterations and modifications which do not depart from the spirit and scope of the invention.

What is claimed is:

1. A restraint for changing an infant comprising:
   a first band having a top surface, a bottom surface, a first end and a second end, and material adapted for enhancing friction therewith with respect to a surface to which said first band is attached, attached to said bottom surface of said first band proximate said first end of said first band and said second end of said first band, and intermediate said first and second ends, respectively;
   a second band longitudinally elastically extendable having a first end and a second end, said first end of said second band attached to said top surface of said first band;
   first hook and loop fastener material attached to said top surface of said first end of said first band;
   second hook and loop fastener material attached to said bottom surface of said second end of said first band for receiving said first hook and loop fastener material;
   third hook and loop fastener material attached to said top surface of said first band a distance from the attachment of said first end of said second band to said top surface of said first band slightly less than a length of said second band from attachment to said first band to said second end of said second band; and
   fourth hook and loop fastener material attached at said second end of said second band for receiving said third hook and loop fastener material.

2. The invention of claim 1, said first end of said first band defining at least two members and said second end of said first band defining at least two members corresponding to and for engaging said at least two members defined by said first end of said first band.

3. The invention of claim 1, wherein said second band has a width slightly less than the length of a midsection of an infant.

4. The invention of claim 1, wherein said second band has a width of about six inches.

5. The invention of claim 1, wherein said first band and said second band are about the same width.

6. The invention of claim 1, wherein said first band and said second band have a width of about six inches.

7. The invention of claim 1, said second band further comprising a layer of rigid fabric material for preventing widthwise deformation of said second band.

8. The invention of claim 7, said rigid fabric material comprising polyester.

9. The invention of claim 1, further comprising a first widthwise transverse strip of rigid material proximate the attachment of said first end of said second band and said top surface of said first band and a second widthwise transverse strip of rigid material proximate said third hook and loop fastener material.

10. The invention of claim 1, said material adapted for enhancing friction therewith with respect to a surface to which said first band is attached comprising corrugated material.

11. The invention of claim 10, said corrugated material comprising vinyl-dotted fabric.

12. A restraint for changing an infant comprising: a first band having a top surface, a bottom surface, a layer of padding material between said top surface and said bottom surface of said first band, a first end and a second end, and material adapted for enhancing friction therewith with respect to a surface to which said first band is attached, attached to said bottom surface of said first band proximate said first end of said first band and said second end of said first band, and intermediate said first and second ends, respectively;
   a second band having a top surface, a bottom surface, at least one longitudinally-extending plastic band between said top surface and said bottom surface of said second band, a layer of flexible but rigid fabric between said top surface and said bottom surface of said second band, a layer of padding material between said top surface and said bottom surface of said second band, and having a first end and a second end, said first end of said second band attached to said top surface of said first band;
   first hook and loop fastener material attached to said top surface of said first end of said first band;
   second hook and loop fastener material attached to said bottom surface of said second end of said first band for receiving said first hook and loop fastener material;
   third hook and loop fastener material attached to said top surface of said first band a distance from the attachment of said first end of said second band to said top surface of said first band slightly less than a length of said second band from attachment to said first band to said second end of said second band;
   fourth hook and loop fastener material attached at said second end of said second band for receiving said third hook and loop fastener material; and
   a first widthwise transverse strip of rigid material proximate the attachment of said first end of said second band and said top surface of said first band and a second widthwise transverse strip of rigid material proximate said third hook and loop fastener material.

13. The invention of claim 12, said first end of said first band defining at least two members and said second end of said first band defining at least two members corresponding to and for engaging said at least two members defined by said first end of said first band, said padding material between said top surface and said bottom surface of said first band comprising bonded polyester, said flexible but rigid fabric comprising non-woven, fused fabric, said padding material between said top surface and said bottom surface of said second band comprising bonded polyester, and said material adapted for enhancing friction therewith with respect to a surface to which said first band is attached comprising vinyl-dotted fabric.

14. A restraint for changing an infant comprising:

- a first band having a top surface, a bottom surface, a first end and a second end, said bottom surface defining at least one first corrugated area adapted for enhancing friction between said bottom surface of said first band and surface of an article to which said first band is applied;
- a second band elastically extendable having a first end and a second end, said first end of said second band attached to said top surface of said first band, and having a layer of substantially rigid polyester fabric material adapted for preventing widthwise deformation of said second band; and
- means for removably attaching said first end of said first band to said second end of said first band.

* * * * *